United States Patent
Takenaka et al.

(10) Patent No.: US 7,512,214 B2
(45) Date of Patent: Mar. 31, 2009

(54) RADIOGRAPHY APPARATUS, RADIOGRAPHY SYSTEM, AND CONTROL METHOD THEREOF

(75) Inventors: Katsuro Takenaka, Saitama-ken (JP); Tadao Endo, Saitama-ken (JP); Toshio Kameshima, Saitama-ken (JP); Tomoyuki Yagi, Saitama-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/875,598

(22) Filed: Oct. 19, 2007

(65) Prior Publication Data

US 2008/0049900 A1 Feb. 28, 2008

Related U.S. Application Data

(63) Continuation of application No. 11/346,873, filed on Feb. 2, 2006, now Pat. No. 7,302,039.

(30) Foreign Application Priority Data

Feb. 24, 2005 (JP) ............................. 2005-049110

(51) Int. Cl.
*H05G 1/64* (2006.01)
(52) U.S. Cl. ............... 378/98.12; 378/98.8; 250/370.09
(58) Field of Classification Search ................ 378/98.8, 378/98.12, 207; 250/208.1, 370.09, 370.11
See application file for complete search history.

(56) References Cited

U.S. PATENT DOCUMENTS

| 6,333,963 | B1 | 12/2001 | Kaifu et al. |
| 6,696,687 | B1 | 2/2004 | Tomisaki et al. |
| 7,302,039 | B2 * | 11/2007 | Takenaka et al. ......... 378/98.12 |
| 7,381,964 | B1 * | 6/2008 | Kump et al. ............ 250/370.11 |

FOREIGN PATENT DOCUMENTS

JP 2002-301053 A 10/2002

* cited by examiner

*Primary Examiner*—Jurie Yun
(74) *Attorney, Agent, or Firm*—Canon U.S.A., Inc. I.P. Division

(57) ABSTRACT

A radiography apparatus includes a conversion unit having conversion elements arranged in a row-column pattern. In an object-image reading operation, the conversion unit detects an object image based on illuminated radiations, and a drive circuit drives the conversion unit so as to allow the conversion unit to output a signal based on the object image. In an offset-data reading operation, the conversion unit detects offset data in a period when the radiations are not illuminating, and the drive circuit drives so as to allow the conversion unit to output a signal based on the offset data. When the numbers of lines driven concurrently in the object-image reading operation is represented by n (equal to 1 or greater) and the numbers of lines driven concurrently in offset-data reading operation is represented by m, the drive circuit controls the conversion unit so as to satisfy the expression: n<m.

7 Claims, 13 Drawing Sheets

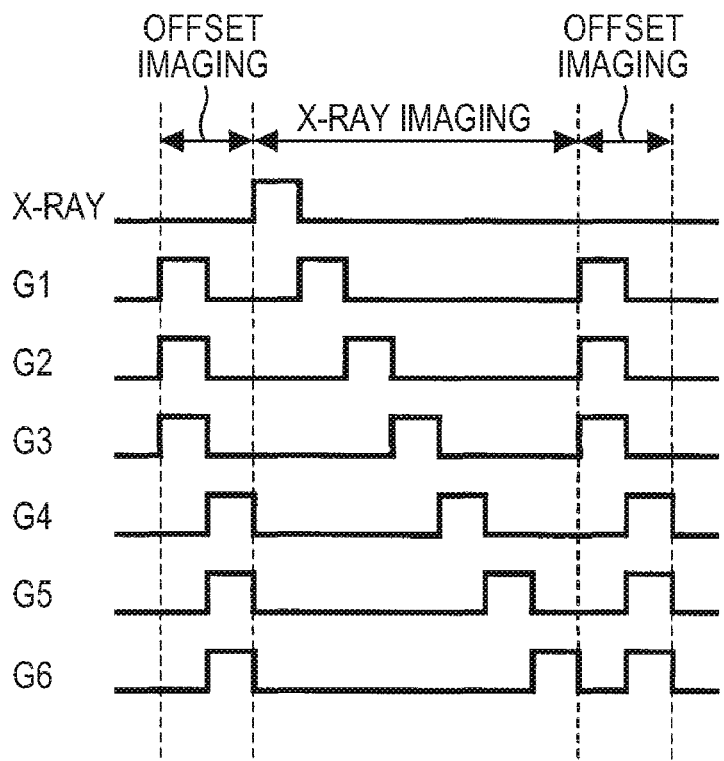
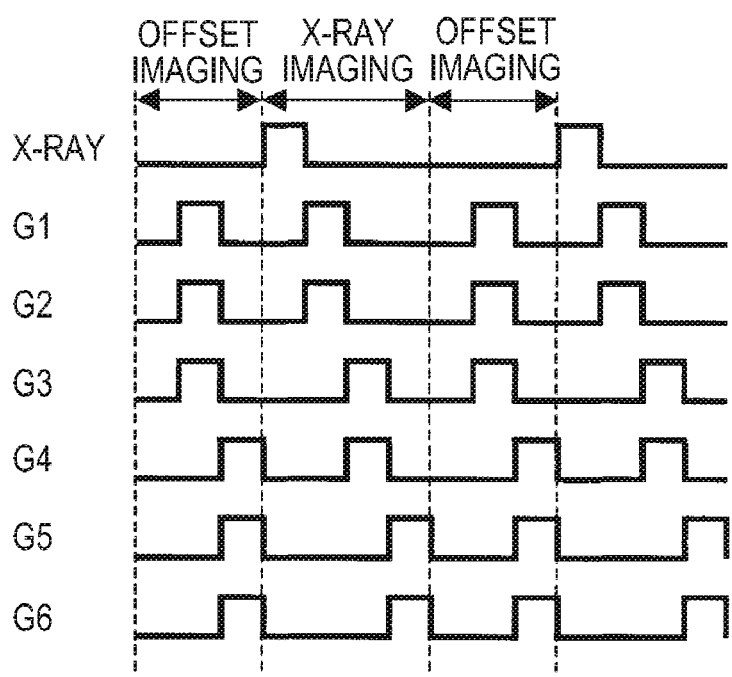

NORMAL IMAGING

PIXEL ADDITION IMAGING

RADIOGRAPHY APPARATUS, RADIOGRAPHY SYSTEM, AND CONTROL METHOD THEREOF

CROSS REFERENCE TO RELATED APPLICATIONS

This application is a continuation of U.S. application Ser. No. 11/346,873, filed Feb. 2, 2006, which claims the benefit of Japanese Application No. 2005-049110 filed Feb. 24, 2005, which are hereby incorporated by reference herein in their entirety.

BACKGROUND OF THE INVENTION

1. Field of the Invention

The present invention relates to a radiography apparatus.

2. Description of the Related Art

Conventionally there exists a medical X-ray still-image capturing system, where X-rays illuminate a patient, and the transmitted X-ray image is exposed on a film. Films are available worldwide, are light and easy to handle, serve to display and store information, can be made so as to have a larger area, and can have a high gray scale range. However, film requires a developing step, a storage place for a long period of time, and time and work for retrieval.

A conventional moving-image capturing system includes an image intensifier (hereinafter, abbreviated to I.I.) is in the mainstream. The I.I. is generally highly sensitive (e.g., from using photomultipliers) and thus advantageous from the viewpoint of a lower required exposed dosage. However, the I.I. distorts a peripheral image, from a typically attached optical system, has low contrast, and is large in size. With the I.I, not only a fluoroscopic image of a patient is monitored by a medical doctor, but also an analog output of a charge-coupled device (CCD) is digitalized so as to be recorded, displayed, and stored. However, since high gray scale is used for medical diagnosis, even when the I.I. is used for capturing a fluoroscopic image, a film is often used for capturing a still image.

A demand for digitalizing an X-ray image in hospital has recently increasing. In order to satisfy this demand, in place of a film, a radiography apparatus (i.e., a flat panel detector (FPD)) having a structure in which an X-ray detecting element has image capturing elements arranged in a two-dimensional pattern is used and an X-ray dose is converted into an electrical signal. Since this allows an X-ray image to be replaced with digital information, image information can be instantly transmitted remotely. Hence, a patient even residing in a local area can enjoy a high level of diagnosis equivalent to that in a university hospital located in the heart of a city, while the filmless operation saves a film-storing space in a hospital. If an excellent image-processing technique can be introduced, an automatic diagnosis with the aid of a computer and without diagnosis of a medical doctor is possibly.

In recent years, a radiography apparatus (a flat panel detector) including image-capturing elements, each composed of a non-monocrystalline thin-film semiconductor such as an amorphous-silicon and capable of capturing a still image has been commercialized. With the technique for preparing a non-monocrystalline thin-film semiconductor, the detector having an area greater than 40 cm squares, covering the size of a human breast has been achieved. Also, since its preparing process is relatively easy, offering the detector at low price is expected. Besides, since a non-monocrystalline thin-film semiconductor such as an amorphous-silicon can be prepared in a form of a thin sheet of glass having a thickness not greater than 1 mm, the detector has a very thin profile.

Such an X-ray radiography apparatus includes a conversion circuit having a plurality of conversion elements arranged therein in a matrix pattern, each configured to convert X-rays into an electrical signal, and a reading circuit configured to read the electrical signal from the conversion circuit.

FIG. 10 illustrates the two-dimensional circuit configuration of a known conversion apparatus. The conversion apparatus includes a photoelectric conversion circuit unit 701 and a reading circuit 702. The photoelectric conversion circuit unit 701 includes photoelectric conversion elements S1-1 to S3-3 serving as conversion elements, switching elements (thin film transistors (TFTs)) T1-1 to T3-3, gate wiring lines G1 to G3 configured to turn on-off the TFTs, signal wiring lines M1 to M3, and a wiring line Vs biased by a power supply Vs and configured to apply an accumulation bias on each of the photoelectric conversion elements. Also, the conversion apparatus includes a shift register SR1 configured to apply a driving pulse voltage on each of the gate wiring lines G1 to G3. A voltage Vg for turning on-off the TFTs is externally supplied.

The reading circuit 702 amplifies outputs of parallel signals of the signal wiring lines M1 to M3 in the conversion circuit unit, converts them into a serial signal, and outputs the serial signal. The reading circuit 702 includes switches RES1 to RES3 configured to reset the signal wiring lines M1 to M3, amplifiers A1 to A3 configured to amplify the signals of the signal wiring lines M1 to M3, sample-and-hold capacitors CL1 to CL3 configured to temporarily store the signals amplified by the amplifiers A1 to A3, switches Sn1 to Sn3 configured to perform sample-and-hold, buffer amplifiers B1 to B3, switches Sr1 to Sr3 configured to convert parallel signals into a serial signal, a shift register SR2 configured to apply a pulse on the switches Sr1 to Sr3 so as to achieve serial conversion, and a buffer amplifier 104 configured to output the serial signal.

An operation of the conversion apparatus shown in FIG. 10 will now be described. FIG. 11 is a timing chart illustrating the operation of a conventional conversion apparatus.

A conversion period (e.g., an X-ray illuminating period) will be described. In a turned-off state of all TFTs, when a light source (e.g., an X-ray source) is turned on in a pulsating way, with a wavelength converter (not shown), radiations are converted into light having wavelengths in a wavelength range allowing the photoelectric conversion elements to be sensitive to the light. The light illuminates each of the photoelectric conversion elements, and signal charges corresponding to the quantity of the light are accumulated in respective element capacitors. If the conversion elements are sensitive to the particular radiation source (e.g., X-rays), the wavelength converter can be removed, and the signal charges corresponding to the dose of the radiation source can be accumulated by the conversion elements. Even after turning off the light source, the signal charges subjected to photoelectric conversion are held in the element capacitors.

A reading period will be described. A reading operation is sequentially performed in order from the photoelectric conversion elements S1-1 to S1-3 in the first line, S2-1 to S2-3 in the second line, and to S3-1 to S3-3 in the third line. First, in order to read the photoelectric conversion elements S1-1 to S1-3 in the first line, the shift register SR1 applies a gate pulse on the gate wiring line G1 of the switching elements (TFTs) T1-1 to T1-3. With this operation, the switching elements T1-1 to T1-3 are turned on, and the signal charges accumulated in the photoelectric conversion elements S1-1 to S1-3 are transferred to the signal wiring lines M1 to M3. Since the signal wiring lines M1 to M3 have reading capacitors CM1 to CM3 added thereto, the signal charges are transferred to the reading capacitors CM1 to CM3 via the corresponding TFTs. For example, the reading capacitor CM1 added to the signal wiring line M1 has a capacitance equal to the total sum (corresponding to three capacitances) of capacitances (Cgs) between gate and sources electrodes of the TFTs T1-1 to T3-1 connected to the signal wiring line M1. The signal charges transferred to the signal wiring lines M1 to M3 are amplified by the amplifiers A1 to A3 respectively. The amplified signals are transferred to and held in the capacitors CL1 to CL3 while turning off an SMPL signal.

Subsequently, when the shift register SR2 applies a pulse on the switches Sr1, Sr2, and Sr3 in that order, the signals held in the capacitors CL1 to CL3 are outputted from the buffer amplifier 104 in order from the capacitors CL1, CL2, and CL3. Since analogue signal outputs of the buffer amplifiers B1, B2, and B3 are outputted from the buffer amplifier 104, the shift register SR2 and the switches Sr1 to Sr3 are collectively called an analogue multiplexer. As a result, photoelectric conversion signals of the photoelectric conversion elements S1-1, S1-2, and S1-3 corresponding to one line are sequentially outputted from the multiplexer. Reading operations of the photoelectric conversion elements S2-1 to S2-3 in the second line and S3-1 to S3-3 in the third line are likewise performed.

When signals of the reading capacitors CM1 to CM3 are sample-held in the capacitors CL1 to CL3 with the SMPL signal for the first line, the reading capacitors CM1 to CM3 are reset at a GND potential with a CRES, and a gate pulse of the gate wiring line G2 is then applied. In other words, during a serial conversion of signals in the first line with the shift register SR2, signal charges of the photoelectric conversion elements S2-1 to S2-3 in the second line are concurrently transferred by the shift register SR1.

With the above-described operation, signal charges of all photoelectric conversion elements in the first to third lines can be outputted. In the foregoing operation of the photoelectric conversion circuit, an X-ray image can be read, however, the actually read image includes an offset generated in the photoelectric conversion circuit and the reading circuit.

The offset is generated due mainly to the following two factors: (A) a dark current of each of the conversion elements, and (B) an offset voltage of each of the amplifiers (e.g., A1 to A3) of the reading circuit. Since an X-ray illuminated image includes an offset component, the offset component can be removed. This removing operation is called an offset correction.

In the case of capturing a still image, the offset correction is performed such that a single sheet of an X-ray-illuminated image is first captured, then, a single sheet of an offset image having no X-rays illuminated thereon is captured, and the offset image is taken out from the X-ray image. Offset imaging is conducted in the same way as X-ray radiographing (i.e., X-ray imaging), except instead of multiple X-ray images one of the images is due to illumination without X-rays. In other words, offset components for all of the pixels must be read to obtain an offset for a single sheet. The foregoing technique is disclosed in U.S. Pat. No. 6,333,963.

In the case of capturing a moving image, the following two methods are offered. According to one method (a continuous imaging method), a sheet of offset image without illumination of X-rays is first captured, then, X-ray capturing is continuously performed, and the X-ray images are corrected with the previously captured offset images. According to the other method (an intermittent imaging method), an X-ray image and an offset image are alternately captured, and the X-ray image is corrected by taking out the offset image therefrom on a basis of its capturing operation. The former presents a high frame rate since only a single sheet of an offset image is captured and, thereafter, allows X-ray images to be continuously captured. However, the latter method has a low frame rate (half the high frame rate) since an X-ray image and an offset image are alternately captured.

Unfortunately, the case of capturing a moving image currently has the additional feature of an offset fluctuating over time. The fluctuation is discussed in Japanese Patent Laid-Open No. 2002-301053. Here, this feature will be described. According to the description of the foregoing patent document, upon capturing a moving image, especially upon capturing a fluoroscopic image, an offset varies every image capturing operation, causing deterioration in image quality. The foregoing patent document discussed the use of an intermittent imaging method as a countermeasure against the fluctuation of an offset, in which X-ray imaging and offset imaging operations are alternately performed so as to update the offset image.

FIGS. 12A to 12D illustrate a timing chart of a control method discussed in the foregoing patent document, wherein the time axis extends horizontally. The contents of the control method will be briefly described below. First, with "FPD collection" (i.e., collection of X-ray image data), X-rays illuminate an object and are captured in an X-ray image. With "collection of calibration data" (i.e., offset imaging"), offset data is captured, added to previously collected offset data (not shown), the summed offset data is averaged, and the averaged offset data is updated as new offset data. Then, with repeated "FPD collection", an image of the X-ray illuminated object is captured and undergoes an offset correction by the updated offset data. As described above, by alternately performing "FPD collection" and "collection of calibration data", offset data is updated as needed so as to inhibit fluctuation of an offset.

While inhibiting fluctuation of an offset as described above, the intermittent imaging method has a low frame rate.

As a method for increasing the frame rate, a pixel addition method is offered. FIGS. 13A and 13B are timing charts illustrating the contents of the pixel addition method, where FIG. 13A illustrates a normal imaging method in which the three gate wiring lines G1 to G3 shown in FIG. 10 are increased to six wiring lines G1 to G6, and FIG. 13B illustrates an example operation of the pixel addition. The pixel addition refers to a method of concurrently reading signals in a plurality of lines. In FIG. 13B, two gate wiring lines are concurrently turned on, and signals corresponding to the two lines are concurrently outputted. With this method, a reading time is reduced by half and a frame rate is increased by double. However, concurrently outputting signals corresponding to the two lines makes an area of a single pixel double, causing a reduced resolution. While the pixel addition is performed by concurrently turning on the two gate lines in the example shown in FIGS. 13A and 13B, the frame rate can be made triple or quadruple by increasing the number of the gate lines to be turned on to three or four.

As described above, the continuous imaging method has a deterioration in image quality while having a high frame rate, and the intermittent imaging method has a low frame rate while inhibiting fluctuation of an offset. In particular, when a non-single crystal semiconductor, such as amorphous silicon, is used in switching elements, the frame rate is considerably reduced since the transfer time of the switching elements is long. In addition, the pixel-addition method has a low resolution while having a high frame rate.

SUMMARY OF THE INVENTION

At least one exemplary embodiment is directed to a radiography apparatus comprising a conversion circuit unit including a plurality of conversion elements arranged in a row-column pattern and configured to convert radiations into an electrical signal, and a drive circuit configured to control the driving of the conversion circuit unit. In an object-image reading operation, the conversion circuit unit detects an object image based on illuminated radiations, and the drive circuit drives the conversion circuit unit so as to allow the conversion circuit unit to output a signal based on the object image. In an offset-data reading operation, the conversion circuit unit detects offset data in a period when the radiations are not illuminating, and the drive circuit drives the conversion circuit unit so as to allow the conversion circuit unit to output a signal based on the offset data. When the numbers of lines driven concurrently by the drive circuit in the object-image reading operation is represented by n (equal to 1 or greater) and the numbers of lines driven concurrently by the drive circuit in offset-data reading operation is represented by m, the drive circuit controls the conversion circuit unit so as to satisfy the expression: n<m. The radiography apparatus further comprises a signal-processing unit configured to process the electrical signal outputted from the conversion circuit unit. The signal-processing unit includes an offset generating unit configured to generate the offset data from the signal, and the offset generating unit corrects the offset data such that the accumulation time of the offset image agrees with that of the object image.

Further features of the present invention will become apparent from the following description of exemplary embodiments with reference to the attached drawings.

BRIEF DESCRIPTION OF THE DRAWINGS

FIG. 7 is a timing chart illustrating an operation of a radiography apparatus according to a second exemplary embodiment.

FIG. 8 is a timing chart illustrating an operation of a radiography apparatus according to a third exemplary embodiment.

DESCRIPTION OF THE EXEMPLARY EMBODIMENTS

Figure 1:
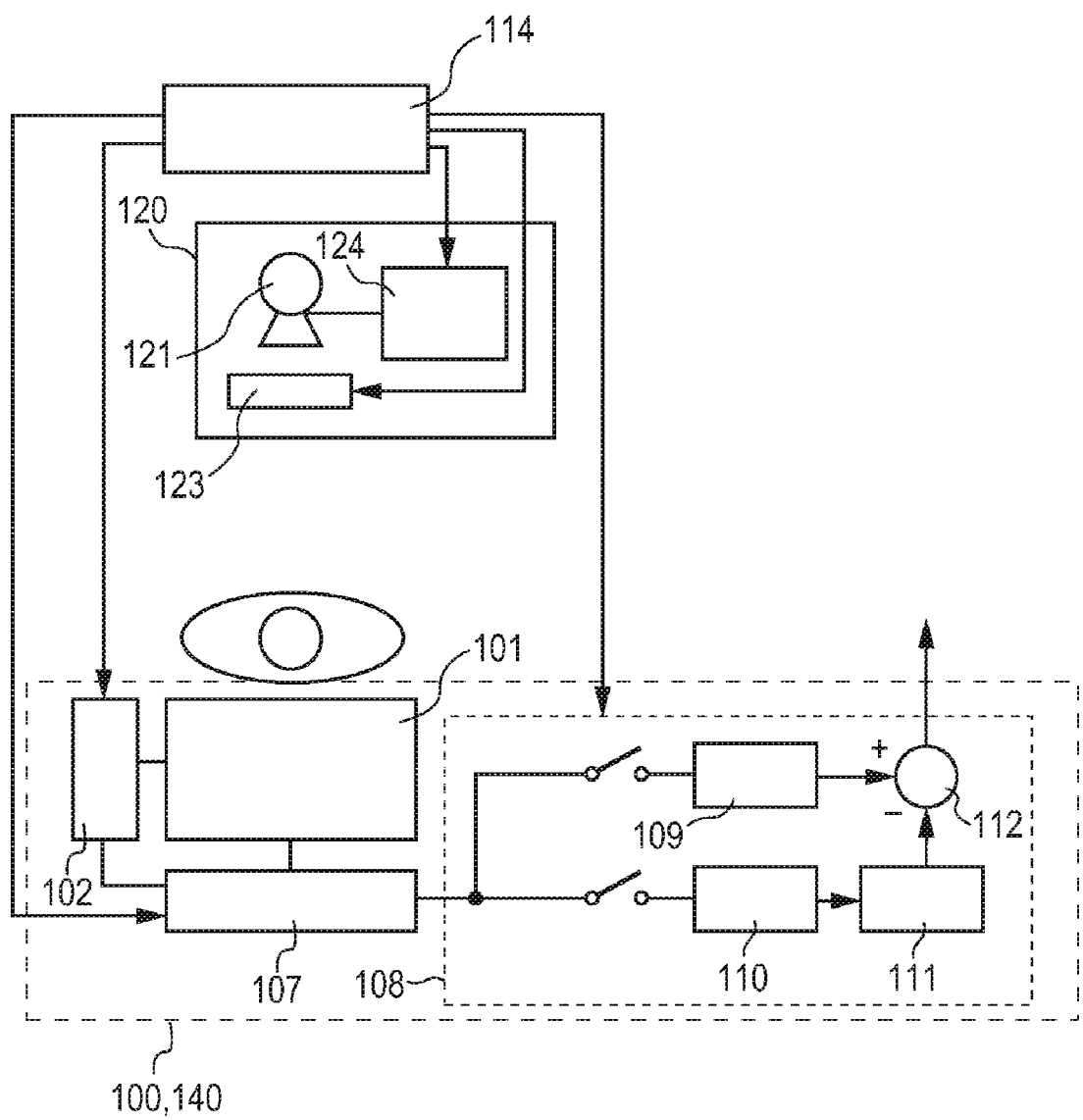
FIG. 1 is a block diagram of a radiography apparatus according to a first exemplary embodiment.

The following description of exemplary embodiment(s) is/are merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example, certain circuitry for signal processing, reading, displaying, and others may not be discussed in detail. However these systems and the methods to fabricate these system as known by one of ordinary skill in the relevant art is intended to be part of the enabling disclosure herein where appropriate.

Note that similar reference numerals and letters refer to similar items in the following figures, and thus once an item is defined in one figure, it may not be discussed for following figures.

Exemplary embodiments will be concretely described with reference to the attached drawings.

First Exemplary Embodiment

Figure 2A:
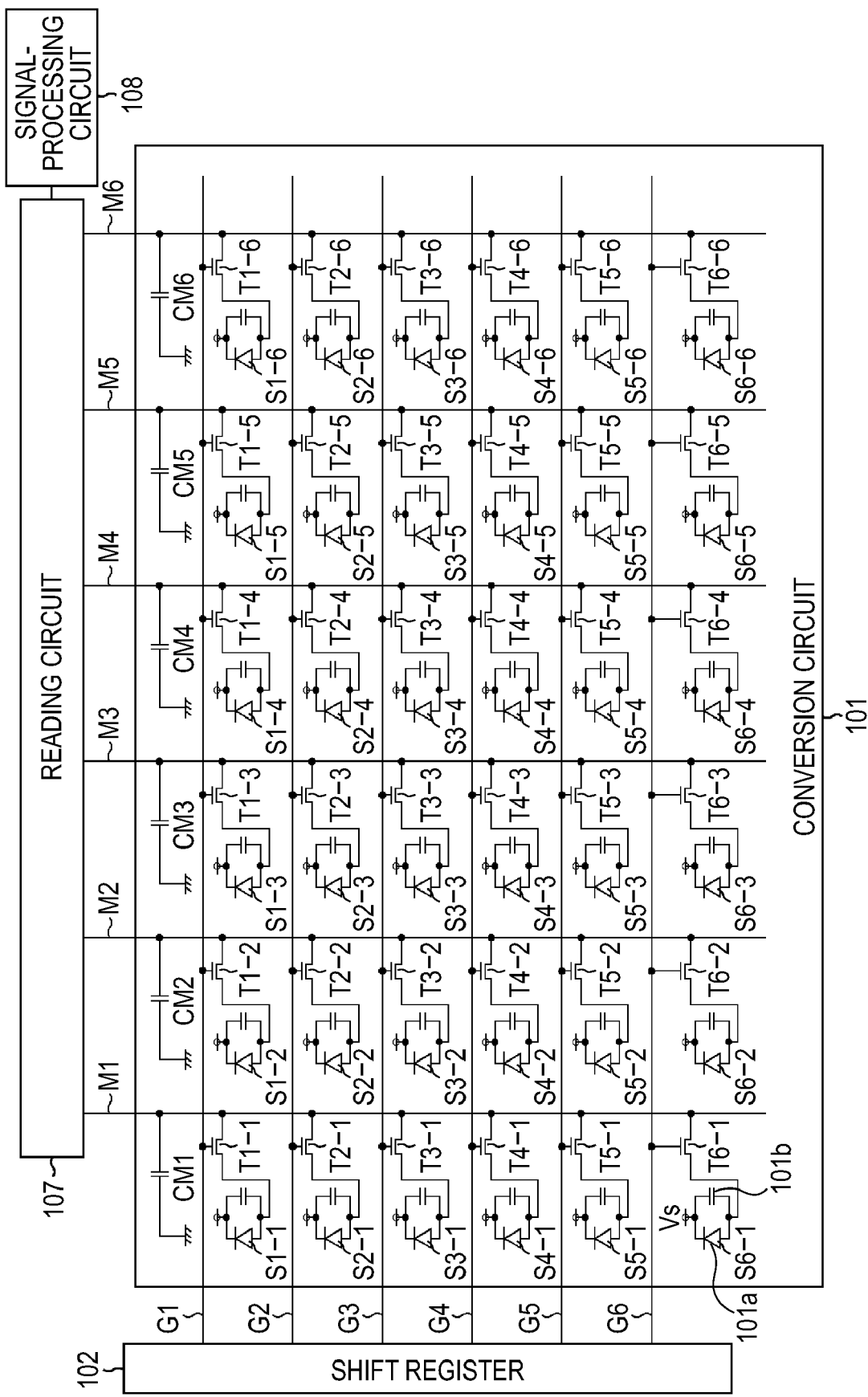
FIG. 2A illustrates the two-dimensional circuit configuration of the radiography apparatus according to the first exemplary embodiment.

A first exemplary embodiment will be described. FIG. 1 is a block diagram of a radiography apparatus according to the first exemplary embodiment. FIG. 2A illustrates the two-dimensional circuit configuration of the radiography apparatus according to the first exemplary embodiment, wherein 36 (=6×6) pixels are illustrated for the sake of simple explanation, however actual exemplary embodiments are not limited to a specific number of pixels.

In the first exemplary embodiment, a photoelectric conversion element serving as a conversion element (e.g., composed of an amorphous-silicon thin-film semiconductor) so that visible light is captured and converted into an electrical signal. Also, with respect to control modes, moving-image and still-image modes can be selectively set. Exemplary embodiments can also include a method of converting the radiation to visible light (e.g., a phosphor converting X-rays into visible light). While an X-ray radiography apparatus will be described in the present exemplary embodiment, the present invention is not limited to X-rays, and α-rays, β-rays, γ-rays, and other types of radiation (electromagnetic and particle)are included in the category of radiations.

As shown in FIG. 1, a radiography apparatus 100 includes a conversion circuit 101, a drive circuit 102 (e.g., a shift register), a reading circuit 107, and a signal-processing circuit 108. The conversion circuit 101 will be described later in detail with reference to FIG. 2A. The signal-processing circuit 108 includes an image data memory 109 configured to store image data, an offset data memory 110 configured to store offset data, an offset-data generating unit 111 adapted for generating offset data corresponding to a single pixel based on data from the offset data memory 110, and a computing unit 112 adapted for subtracting an output of the offset-data generating unit 111 from an output of the image data memory 109. An X-ray generator 120 includes an X-ray tube 121 and an X-ray aperture 123. The X-ray tube 121 is driven by a high voltage generator 124 controlled by an imaging control unit 214 (FIG. 9) and emits X-ray beams (not shown). The X-ray aperture 123 is driven by an imaging control unit 114 and, according to a change of an imaging area, shapes the X-ray beams so as to reduce unnecessary illumination by X-rays.

The imaging control unit 114 drives the X-ray generator 120 serving as a radiation source and the radiography apparatus 100, based on its instruction, grabs radiographic image data of an object. The grabbed radiographic image data of the object is stored in the image data memory 109. In addition, in a state of not driving the X-ray generator 120, the radiography apparatus 100 is driven by the imaging control unit 114 and grabs offset data. The grabbed offset data is stored in the offset data memory 110, and offset data corresponding to a single pixel is generated by the offset-data generating unit 111 configured to generate data on the basis of data from the offset data memory 110. Applying subtraction processing on the radiographic image data and the generated data corresponding to a single pixel achieves an offset correction, allowing offset-corrected radiographic image data to be obtained. In the present exemplary embodiment, offset data is grabbed in the offset data memory 110 and offset data corresponding to a single pixel is then generated in the offset-data generating unit 111. However, exemplary embodiments are not limited to this configuration. For example, with an another possible configuration, offset data corresponding to a single pixel is first generated on the basis of the grabbed offset data in the offset-data generating unit 111, and the generated offset data corresponding to a single pixel is stored in the offset data memory 110. Also, a memory (not shown) configured to store offset data corresponding to a single pixel generated by the offset-data generating unit 111 according to the present exemplary embodiment can be additionally provided.

FIG. 2A illustrates the two-dimensional circuit configuration of the radiography apparatus according to the first exemplary embodiment. As shown in the figure, photoelectric conversion elements S1-1 to S6-6 are arranged in a matrix pattern, each serving as a conversion element, switching elements (TFTs) T1-1 to T6-6, gate wiring lines G1 to G6 configured to turn on-off the TFTs, and signal wiring lines M1 to M6 constitute the circuit. Each photoelectric conversion element (e.g., S6-1) is represented by a photo diode (e.g., 101a) and a capacitor (e.g., 101b) connected in parallel with each other and has a reverse bias applied thereon. In other words, the cathode electrode side of the photo diode is positively biased. While bias wiring lines are typically common wiring lines, for the sake of simplicity, these are shown as individual ones.

Electric charges generated by the photoelectric conversion elements as a result of photoelectric conversion are accumulated in the respective capacitors. In the present exemplary embodiment, the photoelectric conversion elements S1-1 to S6-6, the switching elements T1-1 to T6-6, the gate wiring lines G1 to G6, the signal wiring lines M1 to M6, and the line Vs are collectively called the conversion circuit (also referred to as the radiation-detecting circuit) 101. The shift register 102 applies a pulse on the gate wiring lines G1 to G6 so as to control the drive of the photoelectric conversion elements S1-1 to S6-6. The reading circuit 107 amplifies outputs of parallel signal of the signal wiring lines M1 to M6 in the conversion circuit 101, converts them into a serial signal and outputs the serial signal. The signal processing circuit 108 processes an electrical signal outputted from the reading circuit 107.

Each of the photoelectric conversion elements includes a wavelength converter on its radiation incident side, configured to convert radiations into light having wavelengths in a wavelength range allowing the photoelectric conversion element to be sensitive to the light. The wavelength converter is composed of a mother material (e.g., selected from the group consisting of $Gd_2O_3$, $Gd_2O_2S$, and CsI) The photoelectric conversion element can be composed of various materials (e.g., composed of amorphous silicon). Also, the photoelectric conversion element can include an element configured to absorb radiations without passing through the wavelength converter and directly converting them into an electrical signal. The element can be composed of various materials (e.g., composed of a material selected from the group consisting amorphous selenium, gallium arsenide, mercury iodide, and lead iodide). Although the photoelectric conversion elements corresponding to 36 (=6×6) are illustrated here by way of example as described above, for the sake of easy illustration, a further larger or smaller number of photoelectric conversion elements can be used in any exemplary embodiment. Additionally any configuration can be used (e.g., non-planar, non-matrix).

Figure 2B:
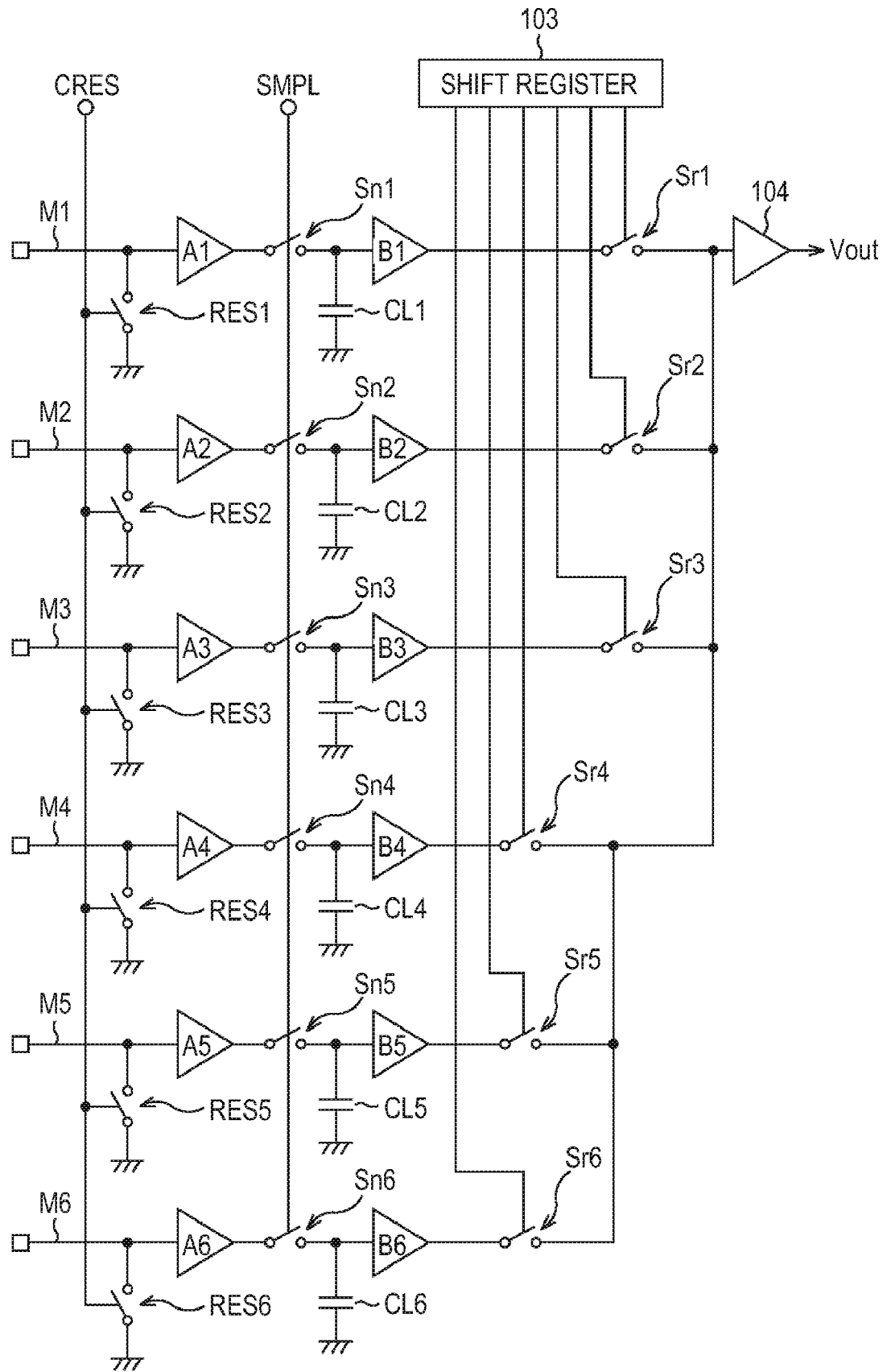
FIG. 2B is a circuit diagram of the internal configuration of a reading circuit of the radiography apparatus.

FIG. 2B is a circuit diagram illustrating the internal structure of the reading circuit 107 shown in FIG. 2A. As shown in FIG. 2B, the reading circuit 107 includes switches RES1 to RES6 configured to reset the signal wiring lines M1 to M6, amplifiers A1 to A6 configured to amplify signals of the signal wiring lines M1 to M6, sample and hold capacitors CL1 to CL6 configured to temporarily store the signals amplified by the amplifiers A1 to A6, switches Sn1 to Sn6 configured to sample-hold the signals, buffer amplifiers B1 to B6, switches Sr1 to Sr6 configured to convert parallel signals into a serial signal, a shift register 103 configured to apply a pulse on the switches Sr1 to Sr6 for achieving a serial conversion, and a buffer amplifier 104 configured to output the serially converted signal.

Figure 3:
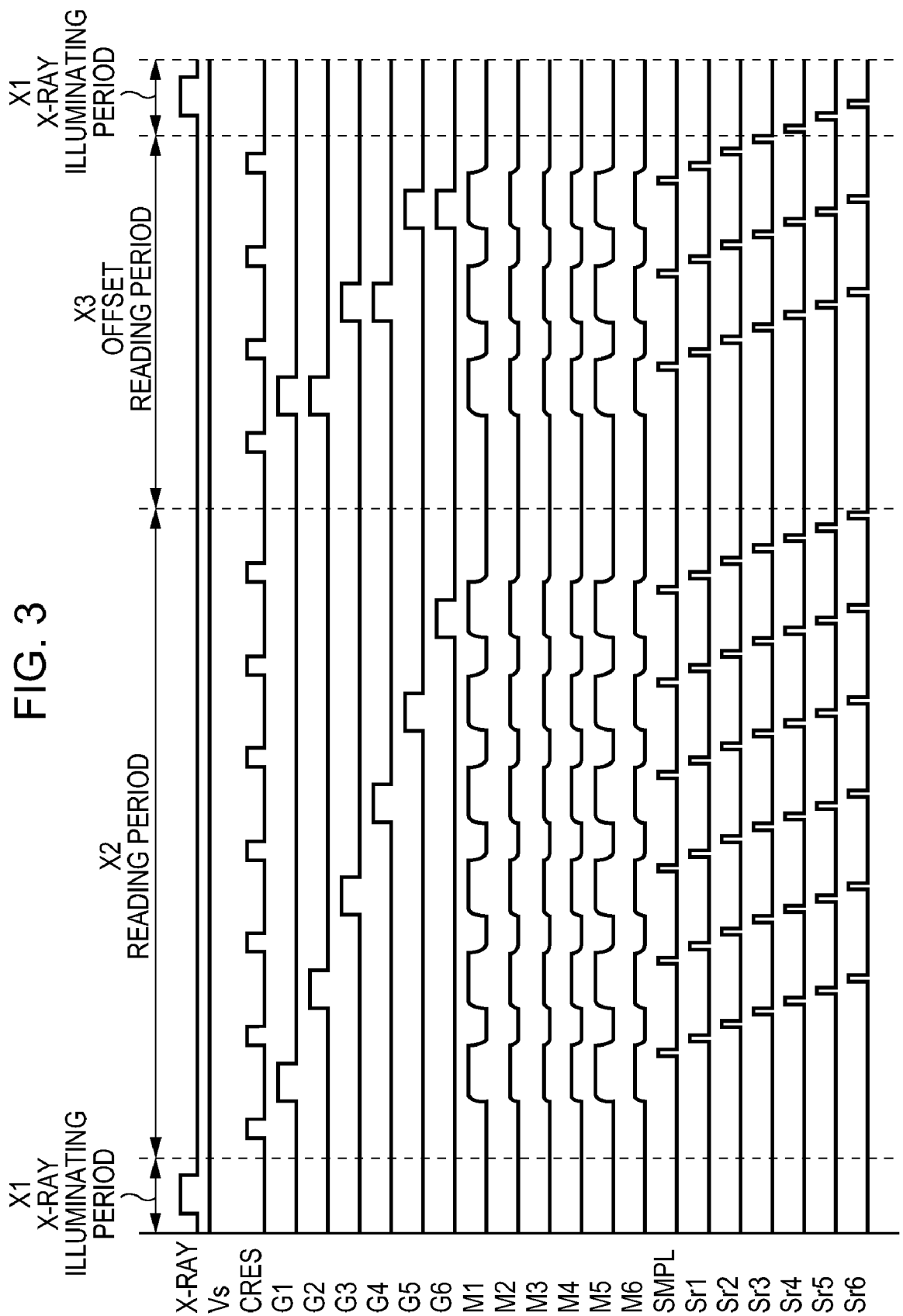
FIG. 3 is a timing chart illustrating a method for driving a photoelectric conversion circuit and the reading circuit.

An operation of the X-ray radiography apparatus having the above-described configuration will be described. FIG. 3 is a timing chart illustrating a method for driving the conversion circuit 101 and the reading circuit 107.

A conversion period X1 (e.g., an X-ray illuminating period) will be described. In a turned-off state of all TFTs, when a light source (e.g., an X-ray source) is turned on in a pulsating way, with a wavelength converter (not shown), radiations are converted into light having wavelengths in a wavelength range allowing the photoelectric conversion elements to be sensitive to the light. The light is illuminated on each of the photoelectric conversion elements, and signal charges corresponding to the quantity of the light are accumulated in respective element capacitors (e.g., 101b). If the conversion elements are sensitive to X-rays, the wavelength converter can be removed, and the signal charges corresponding to the dose of the X-rays are accumulated by the conversion elements. Even after turning off the light source, the signal charges subjected to photoelectric conversion are held in the element capacitors.

A reading period X2 will be described. A reading operation is sequentially performed in order from the photoelectric conversion elements S1-1 to S1-6 in the first line, the photoelectric conversion elements S2-1 to S2-6 in the second line, the photoelectric conversion elements S3-1 to S3-6 in the third line, and so on up to those in the sixth line. First, in order to read the photoelectric conversion elements S1-1 to S1-6 in the first line, a gate pulse is applied on the gate wiring line G1 of the switching elements (TFTs) T1-1 to T1-6 from the shift register SR1. With this operation, the switching elements T1-1 to T1-6 are turned on, and the signal charges accumulated in the photoelectric conversion elements S1-1 to S1-6 are transferred to the signal wiring lines M1 to M6 respectively. Since the signal wiring lines M1 to M6 have reading capacitors CM1 to CM6 added thereto, the signal charges are transferred to the reading capacitors CM1 to CM6 via the corresponding TFTs. For example, the reading capacitor CM1 added to the signal wiring line M1 has a capacitance equal to the total sum (corresponding to six capacitances) of capacitances (Cgs) between gate and source electrodes of the TFTs T1-1 to T6-1 connected to the signal wiring line M1. The signal charges transferred to the signal wiring lines M1 to M6 are amplified by the amplifiers A1 to A6 (FIG. 2B). The amplified signals are transferred to and held in the capacitors CL1 to CL6 (FIG. 2B) while turning off an SMPL signal.

Then, by applying a pulse on the switches Sr1, Sr2, Sr3, Sr4, Sr5, and Sr6 from the shift register 103 in that order, the signals held in capacitors CL1, CL2, CL3, CL4, CL5, and CL6 are outputted from the buffer amplifier 104 in that order. Since analog signals are sequentially outputted from the amplifier 104, the shift register 103 and the switches Sr1 to Sr6 are collectively called an analog multiplexer. As a result, the photoelectric conversion signals of the photoelectric conversion elements S1-1 to S1-6 in the first line are sequentially outputted by the analog multiplexer. Operations of reading the photoelectric conversion signals of the photoelectric conversion elements S2-1 to S2-6 in the second line and S3-1 to S3-6 in the third line, and those in the fourth to sixth lines are likewise performed.

When the signals of the signal wiring lines M1 to M6 are sample-held in the sample and hold capacitors CL1 to CL6 by an SMPL signal of the first line, the signal wiring lines M1 to M6 are reset at a GND potential by a CRES signal, and thereafter, can accept application of a gate pulse of the gate wiring line G2 thereon. In other words, during an operation of an analog multiplexer for serially converting the signal of the first line, the signal charges of the photoelectric conversion elements S2-1 to S2-6 in the second line can be concurrently transferred.

While an X-ray image can be read through the above-described reading operation, an X-ray image having undergone no processing actually includes an offset generated in the conversion circuit and the reading circuit as described above. Hence, in order to remove the offset component, offset imaging is needed.

An offset reading period X3 will be described. During the offset reading period, the offset reading operation is performed without illumination of X-rays. The offset reading period X3 is different from the reading period X2 (e.g., X-ray reading period) only in timings of applying a gate pulse. More particularly, during the X-ray reading period, the switching elements (TFTs) are turned on-off sequentially in order from the gate wiring line G1 to the gate wiring line G6. Whereas, during the offset reading period, a pixel addition is performed such that the switching elements corresponding to two lines, e.g., a combination of the gate wiring lines G1 and G2, G3 and G4, or G5 and G6 are concurrently turned on-off.

While, in the known intermittent imaging method, an offset reading operation is the same as a reading operation performed after illumination of X-rays, in order to shorten the offset reading period X3, the switching elements (TFTs) corresponding to two lines are concurrently turned on. By concurrently turning on two lines, the offset reading period X3 is made half the reading period X2 (e.g., X-ray reading period). As a result, according to the present exemplary embodiment, a time needed for a combination of "an X-ray reading period+ an offset reading period" is made shorter, down to that obtained by multiplying a factor 0.75 to the previously needed one, and accordingly, the frame rate is increased by a factor of about 1.3. In other words, presuming that a time needed for each of the reading operations according to the known intermittent imaging method is 1, the total time needed for the respective reading operations is given by "an X-ray reading time+an offset reading time" (=1+1=2) on one hand, the total time needed for the respective reading operations according to the first exemplary embodiment is given by "an X-ray reading time+an offset reading time" (=1+0.5=1.5) on the other, resulting in a shorter time shorter by a factor of 0.75 (1.5/2) and improving the frame rate by a factor of about 1.3 (2/1.5).

If the number of lines to be concurrently read is increased to, e.g., three or four, the offset reading period can be made further shorter. Hence, the greater the number of pixel addition for an offset reading operation an frame rate achieved by the intermittent imaging method can be made closer to that achieved by the continuous imaging method.

In the first exemplary embodiment, with the intermittent imaging method for alternately performing X-ray imaging and offset imaging operations, fluctuation of an offset is inhibited or reduced.

Since pixel addition is performed, in at least one exemplary embodiment, during the offset imaging operation, X-ray information is not subjected to pixel addition, thereby preventing reduction in resolution.

Figure 4:
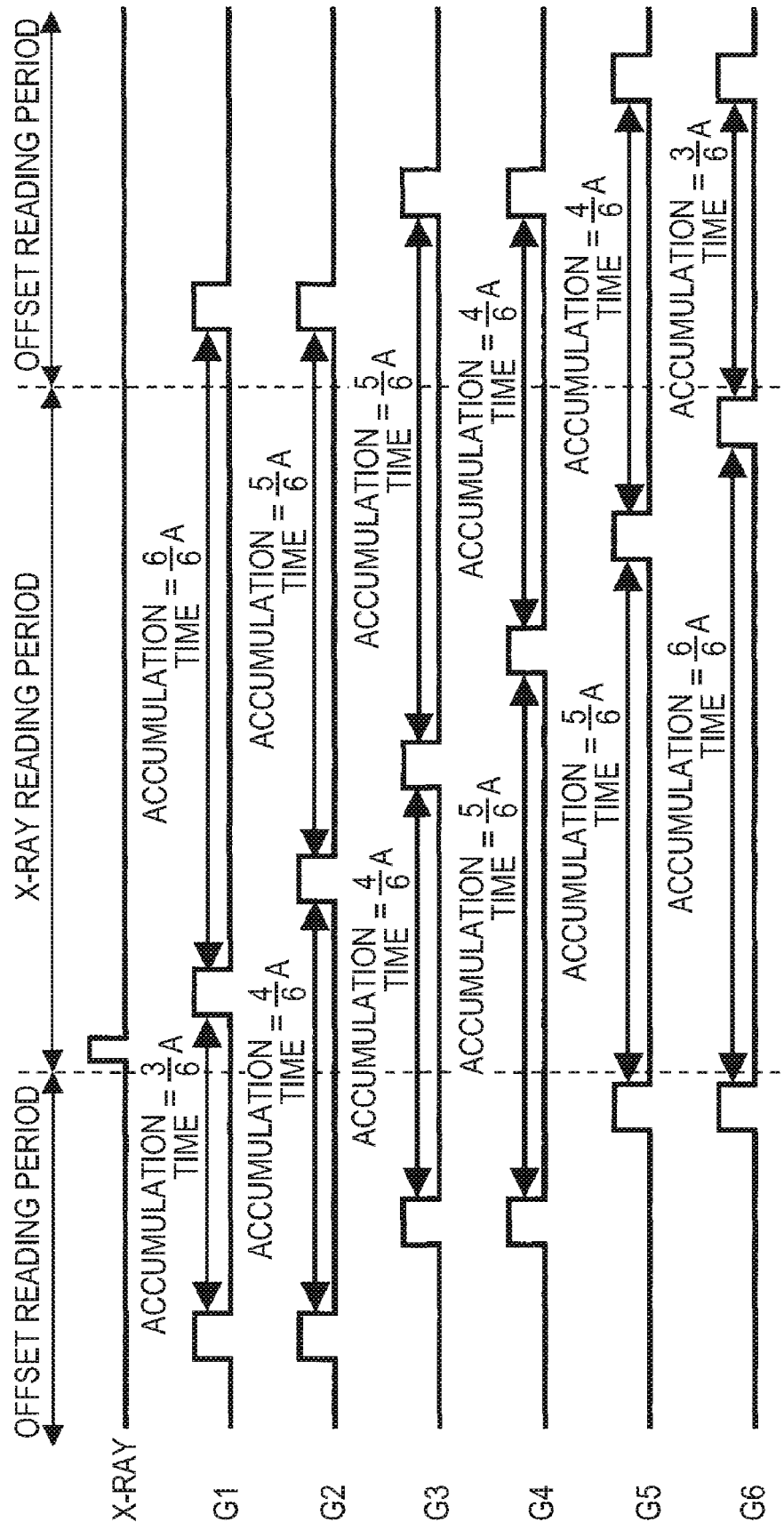
FIG. 4 illustrates a change in accumulation time.

In the meantime, when information of an offset image corresponding to two lines is concurrently read, the information corresponding to two pixels is outputted and therefore needed to be corrected into information corresponding to a single pixel. When pixel addition is performed only for offset reading, an accumulation time of a sensor changes. FIG. 4 illustrates a change in accumulation time. An accumulation time refers to a time from turn-on to turn-off of a TFT. Since a dark electric current of the sensor is accumulated in the sensor, a longer time from turn-on to turn-off of the TFT results in a higher output of the offset due to the accumulated dark electric current. Accordingly, in order to perform pixel addition only for offset reading, two kinds of corrections: one for correcting the output corresponding to two pixels into that corresponding to a single pixel and the other for correcting the accumulated time are needed.

Figure 5:
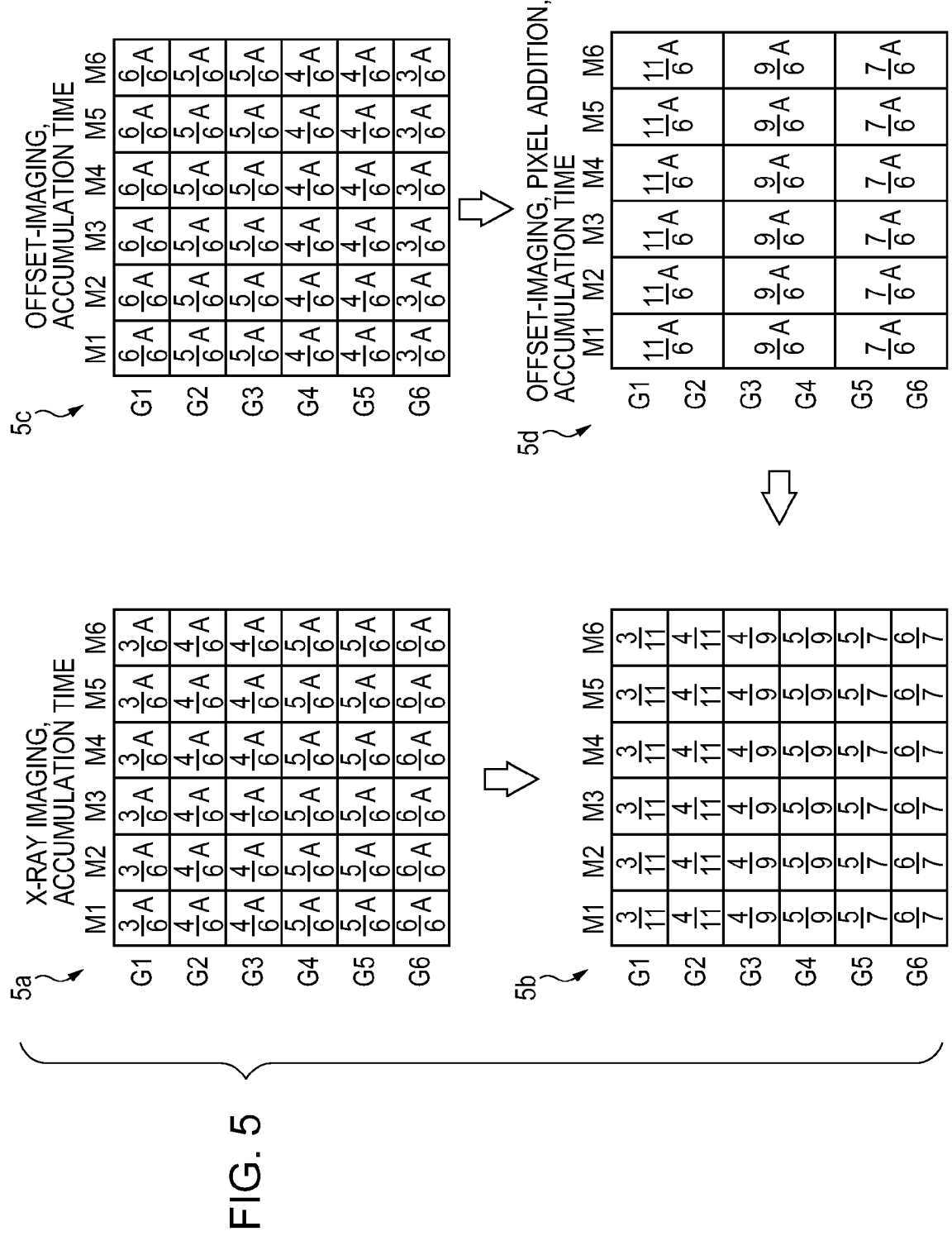
FIG. 5 illustrates a correction of the accumulation time method.

Referring now to FIGS. 1, 4, and 5, the foregoing correction/reduction method will be described. In FIG. 4, gate pulses are indicated by G1 to G6, and a time from turn-on to turn-off of each gate pulse indicates an accumulation time. When an accumulation time in the absence of pixel addition is represented by A, during an X-ray reading period, as the line advances, an accumulation time of the corresponding line becomes longer, for example, accumulation times of the first line (G1) and the second line (G2) are respectively ⅜×A and 4/6×A. During an offset reading period, as the line advances, an accumulation time of the corresponding line becomes shorter, contrary to that during the X-ray reading period, for example, accumulation times, during the reading period (e.g., X-ray reading period) of the first line (G1) and the second line (G2) are respectively 6/6×A and 5/6×A.

FIG. 5 is a picture image illustrating the accumulation times shown in FIG. 4, where the signal wiring lines M1 to M6 are shown in the horizontal direction, and the gate wiring lines G1 to G6 are shown in the vertical direction. In the normal offset correction, in order to remove the offset component, a computation of "subtracting an offset image from an X-ray image" is performed. Whereas, in the first exemplary embodiment, since accumulation times of an X-ray image and an offset image are different from each other, previously correcting the offset image is needed.

As shown in FIG. 5, accumulation times of an X-ray image 5a in the first and second lines G1 and G2 are respectively ⅜×A and 4/6×A, and accumulation times of an offset image 5c in the first and second lines G1 and G2 are respectively 6/6×A and 5/6×A. In addition, since the offset image is subjected to pixel addition, signals in the first and second lines G1 and G2 are concurrently outputted, resulting in the total accumulation time 11/6×A (see image 5d). Hence, in the case of correcting the first line G1, the accumulation time of the offset image can be corrected so as to agree with that of the X-ray image. In the first exemplary embodiment, since the accumulation times of the X-ray image and the offset image are respectively ⅗×A and ¹¹⁄₆×A, by multiplying the accumulation time of the offset image by a factor of ³⁄₁₁, the accumulation time of the offset image is corrected so as to agree with that of the X-ray image (⅗A=¹¹⁄₆A×³⁄₁₁). An accumulation-time correction table (see 5b) for correcting an accumulation time as described above is prepared in the offset-data generating unit 111 An accumulation time is corrected every capturing of an offset image, and thereafter, an offset correction is performed in the computing unit 112.

Figure 6:
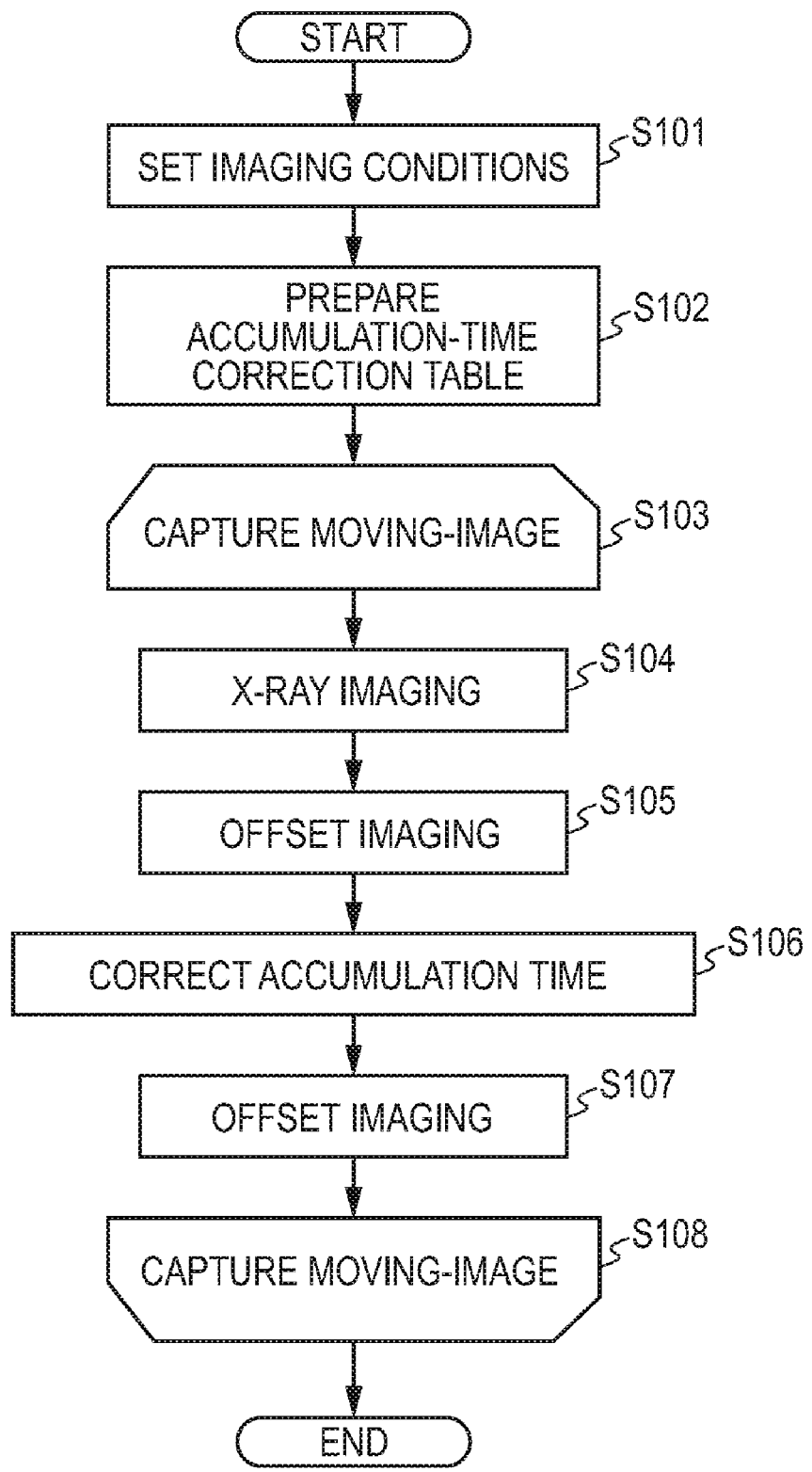
FIG. 6 is a flowchart illustrating a control method of the radiography apparatus according to the first exemplary embodiment.

FIG. 6 is a flowchart illustrating a control method of the radiography apparatus according to the first exemplary embodiment. Upon setting the image-capturing conditions, the number of adding pixels upon capturing an offset image is inputted concurrently with inputting illumination conditions (step S101). Then, on the basis of the inputted number of adding pixels, an accumulation-time correction table (e.g., 5b) is prepared on the basis of the foregoing computations shown as in FIG. 5 (step S102). Subsequently, an actual moving-image is captured (step S103) such that an X-ray image is captured (step S104), and thereafter, an offset image is captured (step S105). Then, an accumulation time correction is applied on the offset image (step S106). Subsequently, by computation of "subtracting an offset image from an X-ray image", an offset correction is performed (step S107). This cycle is repeated until completion of capturing the moving-image (step S108).

Second Exemplary Embodiment

A second exemplary embodiment will be described. The second exemplary embodiment can have the same circuit configuration as that of the first exemplary embodiment. FIG. 7 is a timing chart illustrating timings of an operation of a radiography apparatus according to the second exemplary embodiment.

While, in the first exemplary embodiment, the number of pixels for pixel addition for offset reading is set at two (i.e., two-pixel addition is set), three-pixel addition is set in the second exemplary embodiment. With the three-pixel addition, relative to the corresponding values achieved in the absence of pixel addition, the offset imaging time is reduced by a factor of ⅓, and the frame rate is increased by a factor of 1.5. By increasing the number of adding pixels, e.g., by setting four-pixel addition or five-pixel addition, the frame rate is increased. Accordingly, the number of adding pixels can be determined in response to a necessary frame rate.

Third Exemplary Embodiment

A third exemplary embodiment will be described. The circuit configuration of the third exemplary embodiment can be the same as that of the first exemplary embodiment, along with the second exemplary embodiment. FIG. 8 is a timing chart illustrating an operation of a radiography apparatus according to a third exemplary embodiment.

As shown in FIG. 8, in the third exemplary embodiment, the two-pixel addition is performed upon X-ray imaging and three-pixel addition is performed upon offset imaging. Consequently, the frame rate is increased by a factor of 2.4 with respect to that achieved in the absence of pixel addition. However, in the third exemplary embodiment, the resolution decreases slightly since the pixel addition is performed upon X-ray imaging.

Fourth Exemplary Embodiment

A fourth exemplary embodiment will be described. The circuit configuration of the fourth exemplary embodiment can be the same as that of the first exemplary embodiment along with the first exemplary embodiment. In the fourth exemplary embodiment, the accumulation time correction performed in the first exemplary embodiment is omitted.

In the case of a low frame rate, since a difference in accumulation times is large, e.g., in the approximate range from several tens milli-seconds (ms) to several hundreds ms, the accumulation time correction/reduction can be performed. In the case of a high frame rate, since a difference in accumulation times is small, e.g., about several ms, even omission of the accumulation time correction does not adversely affect an image.

Exemplary Applications

Figure 9:
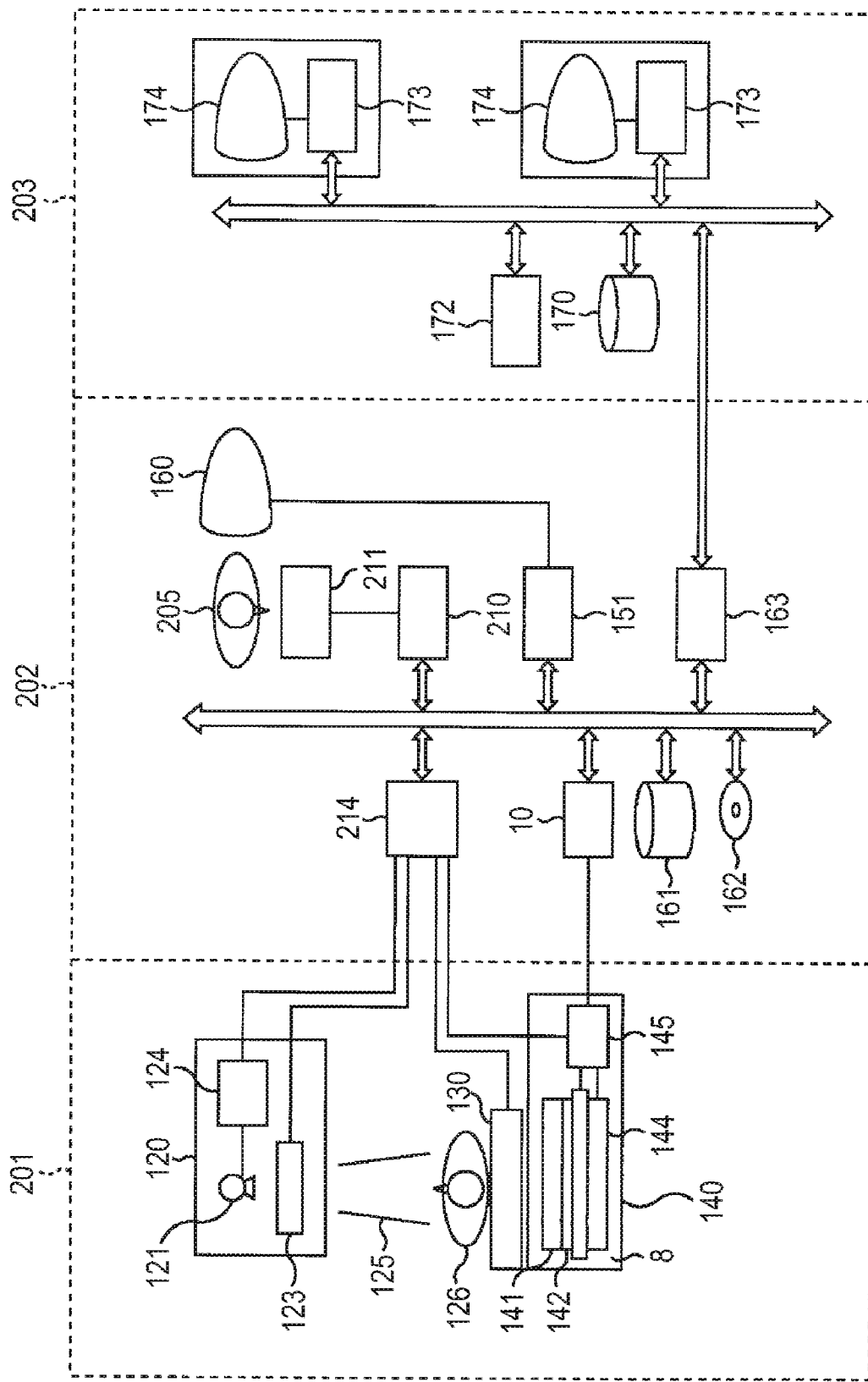
FIG. 9 is a diagrammatic view of the configuration of an X-ray radiography system according to another exemplary embodiment.
Figure 10:
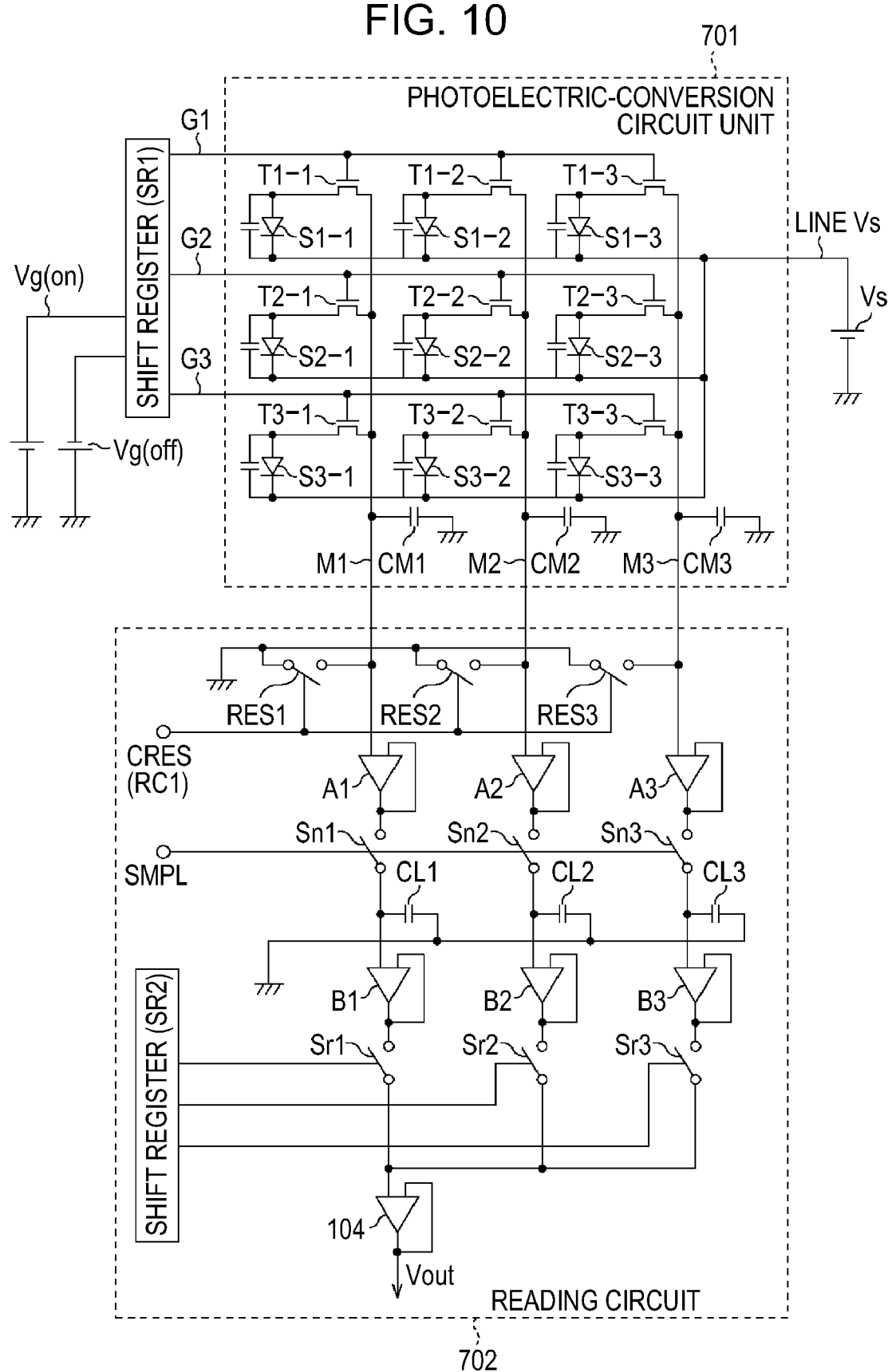
FIG. 10 illustrates the two-dimensional circuit configuration of a conventional conversion apparatus.
Figure 11:
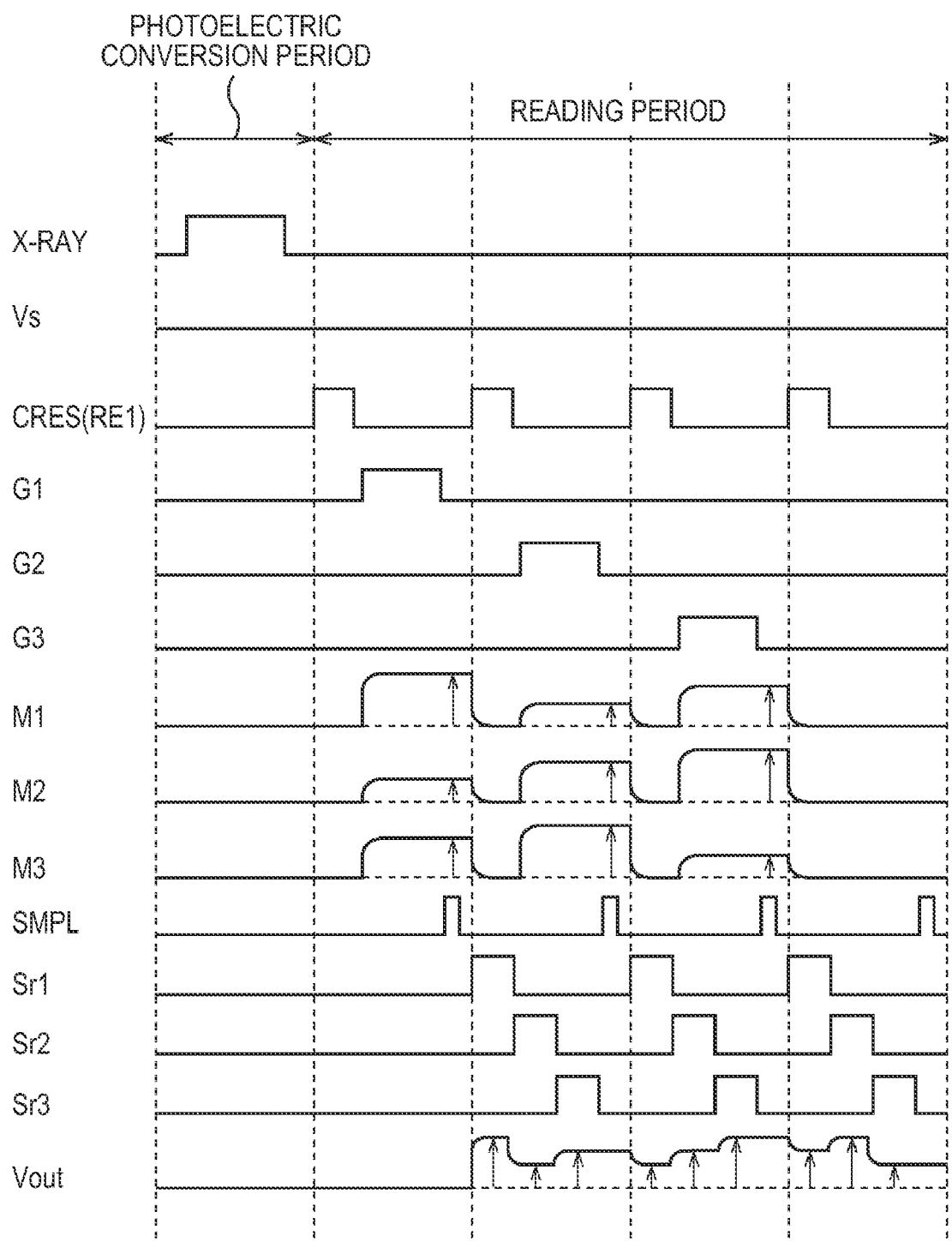
FIG. 11 is a timing chart illustrating an operation of the conventional conversion apparatus.
Figure 12A:
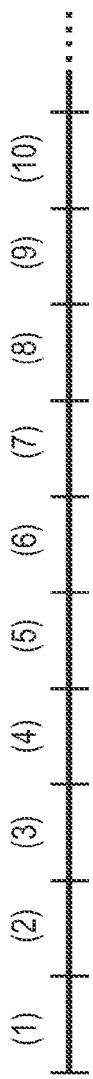
FIGS. 12A-12D are timing charts illustrating a control method of the conventional conversion apparatus.
Figure 12B:
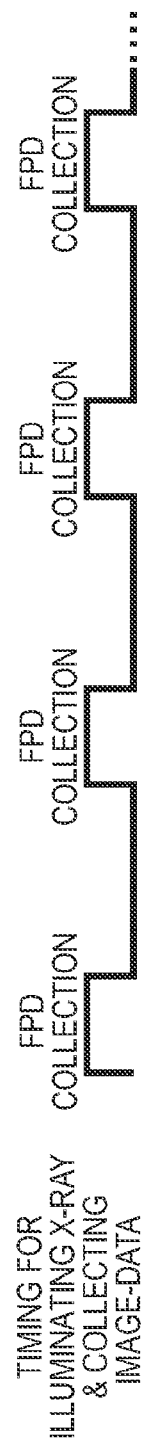
Figure 12C:
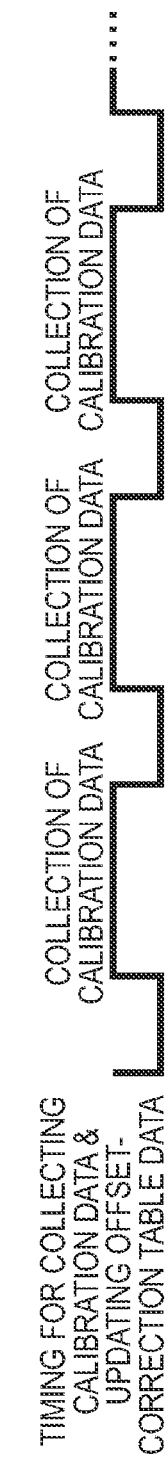
Figure 12D:
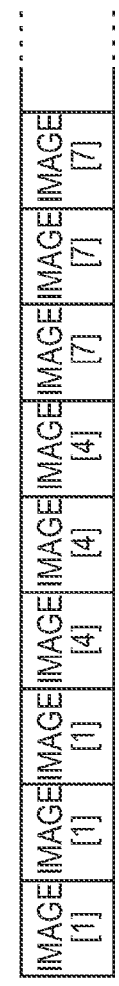
Figure 13A:
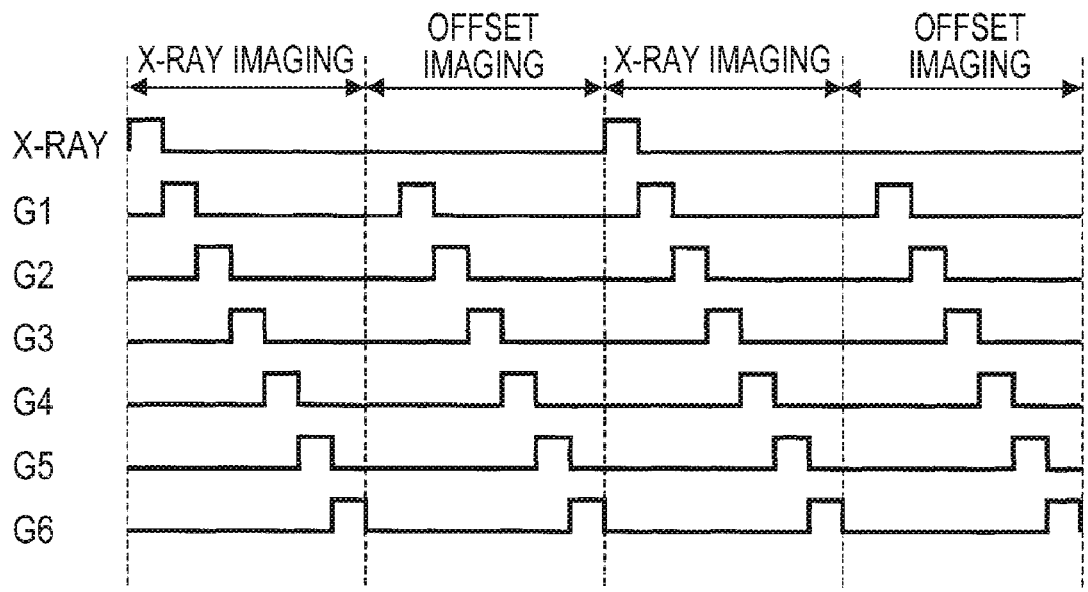
FIGS. 13A and 13B present timing charts illustrating a pixel-addition method.
Figure 13B:
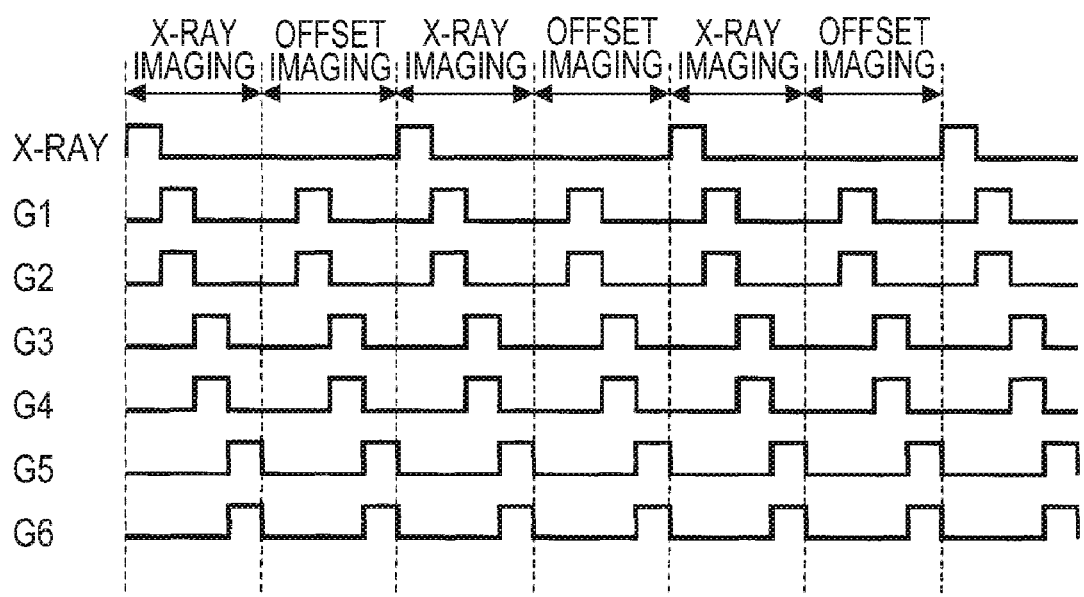

An X-ray radiography system achieving an X-ray radiography method in each of the first to fourth exemplary embodiments will be described. FIG. 9 is a schematic view illustrating the structure of an X-ray radiography system according to another exemplary embodiment. As shown in FIG. 9, the X-ray radiography system can include an X-ray room or system 201, an X-ray control room or system 202, and a diagnosis room or system 203. Note in at least one exemplary embodiment all of the systems (201-203 are in the same room and can be operated by the same computer). Thus, although the following exemplary embodiments may discuss operations taking place in separate room, such discussions are illustrative only and thus the operations can take place in one room, remotely, and/or using the same computer system. An operation of the overall X-ray radiography system can be under control of a system control unit 210 (e.g., equipped in the X-ray control room 202).

As an exemplary operator interface 211 (e.g., in the X-ray control room 202) can include a number of interfaces (e.g., a touch panel on a display, a mouse, a keyboard, a joystick, and a foot switch). With the operator interface 211, the imaging conditions (a still image, a moving image, a tube voltage, a tube current, and radiation time, and so forth), an imaging timing, image-processing conditions, a test object ID, a method for processing a captured image, and so forth can be set. However, since most of these pieces of information are transferred from a radiation information system (not shown), individually inputting them is not needed. An operator can check a captured image. That is, the operator can determine whether an imaging angle is appropriate, a patient does not move, and an image processing is proper.

The system control unit 210 gives an instruction of the imaging conditions depending on an instruction from an operator 205 or the radiation information system (not shown), to the imaging control unit 214 responsible for an X-ray radiography sequence and starts the data-grabbing operation. On the basis of the instruction, the imaging control unit 214 grabs image data by driving the X-ray generator 120 serving as a radiation source, an image-capturing bed 130, and an x-ray radiography apparatus (e.g., a flat panel detector) 140 and transfers the image data to an image-processing unit 10. Thereafter, the system control unit 210 applies an image-processing on the image data, specified by the operator 205, displays the image data on a display 160, and stores raw data in an external storage 161, having undergone a basic-image-processing including an offset correction/reduction and a white noise correction/reduction. In addition, on the basis of the instruction of the operator 205, the system control unit 210 performs a repeated image-processing operation, a playback display operation, transferring and storing operations of image data to and in an apparatus on a network, a display-displaying operation, a printing operation on a film, and so forth.

The description of the X-ray radiography system will be sequentially reinforced while following the flow of a signal. The X-ray generator 120 includes the X-ray tube 121 and the X-ray aperture 123. The X-ray tube 121 is driven by the high voltage generator 124 controlled by the imaging control unit 214 and emits X-ray beams 125. The X-ray aperture 123 is driven by the imaging control unit 214 and, according to a change of an imaging area, shapes the X-ray beams 125 so as to prevent unnecessary illumination by X-rays. The X-ray beams 125 are directed to a test object 126 lying on the transparent X-ray image-capturing bed 130. The image-capturing bed 130 is driven according to the instruction of the imaging control unit 214. The X-ray beams 125 pass through the test object 126 and the image-capturing bed 130 and illuminate the x-ray radiography apparatus 140.

The x-ray radiography apparatus 140 includes a grid 141, a wavelength converter 142, a conversion circuit unit 8, an X-ray dose monitor 144, and a drive circuit 145. The grid 141 reduces influence of X-ray scatter generated due to passing through the test object 126. The grid 141 is composed of radiation absorbing material (e.g., X-ray low-absorbing and high-absorbing members) and can have a stripe structure (e.g., a stripe structure composed of Al and Pb). Upon being illuminated (e.g., by X-rays), according to the instruction of the imaging control unit 214, the grid 141 vibrates so as to prevent generation of moire fringes due to the relationship of the grid ratio between the conversion circuit unit 8 and the grid 141.

The wavelength converter 142, the photoelectric conversion elements array (the conversion circuit unit 8), and the drive circuit 145 are provided so as to serve as components of the digital X-ray radiography apparatus. The wavelength converter 142 can have an exit substance (e.g., phosphor) that can interact with the X-rays (e.g., via recombination) to fluorescence, providing imaging in the visible range. The a exit substance can be of any type that can fluorescence (e.g., $CaWo_4$, $CdWO_4$, a compound of CsI:Tl or Zns:Ag, or a luminance material activated in the substance to fluorescence as known by one of ordinary skill in the relevant art). The wavelength converter 142 can have the conversion circuit unit 8 adjacent thereto. The conversion circuit unit 8 converts photons into an electrical signal. The X-ray dose monitor 144 monitors the quantity of transmitting X-rays. The X-ray dose monitor 144 can be of a type directly detecting X-rays with the aid of a photoreceptor or another type detecting light emitted from the wavelength converter 142.

In the present exemplary embodiment, visible light (the quantity of which is in proportion to an X-ray dose) transmitted through the conversion circuit unit 8 is detected by an amorphous-silicon photoreceptor deposited on the rear surface of the photoelectric conversion circuit unit 8, and information of the detected light is transmitted to the imaging control unit 214. Based on the information, the imaging control unit 214 drives the high voltage generator 124 so as to shut down or adjust illumination of X-rays. The drive circuit 145 includes the reading circuit unit and an A/D converter. The drive circuit 145 drives the conversion circuit unit 8 under control of the imaging control unit 214, reads an analog signal from each pixel, and converts the read analog signal into a digital signal.

An image signal from the X-ray radiography apparatus 140 is transferred from the X-ray room/system 201 to the image-processing unit 10 disposed in the X-ray control room/system 202. On the occasion of this transfer, the level of noise in the X-ray room 201 is sometimes high because of generation of X-rays. Accordingly, the noise sometimes presumably prevents accurate transfer of image data. As a countermeasure against this problem, the transfer path can be arranged so as to have an increased noise proof property. For example, a transfer system including an error-correcting function or a transfer path composed of a twisted shield wire pair made by a differential driver or a transfer path made by an optical fiber can be provided. The image-processing unit 10 changes over display data according to the instruction of the imaging control unit 214. In addition, the image-processing unit 10 can be configured to correct or reduce errors in (an offset correction/reduction and a white noise correction/reduction)image data, perform space filtering, perform recursive processing in real time, perform gray-scale processing, perform scatter (radiation) correction, and a variety of spatial frequency processings.

An image processed by the image-processing unit 10 is displayed on the display 160 via a display adaptor 151. Also, along with the real-time image processing, the basic image having only its data corrected or error reduced is stored in the external storage 161. The external storage 161 can be a data storage having features of a large capacity, high speed, and high reliability, (e.g., a hard disk array of a redundant array of independent disks (RAID)). Image data stored in the external storage 161 can be stored in an external storage 162 according to the instruction of the operator 205. On that occasion, the image data is reconfigured so as to satisfy a predetermined standard (e.g., IS&C) and is then stored in the external storage 162 (e.g., a magnet optical disk). Alternatively, in place of the external storage 162, the image data can be stored in memory (e.g., a hard disk) provided in a file server 170 disposed in the diagnosis room/system 203 and connected to the storage 162 (e.g., via a LAN board 163). With this arrangement, in the diagnosis room/system 203, an image processing terminal 173 facilitates subjecting image data to a variety of processings and displayed on a monitor 174.

The radiography system (the X-ray radiography system) according to the foregoing exemplary embodiments can include the x-ray radiography apparatus 140, the imaging control unit 214, and the image-processing unit 10.

In exemplary embodiments, the photoelectric conversion element serving as a conversion element is not particularly limited to having a particular structure. For example, a photoelectric conversion element configured to be mainly composed of amorphous silicon, to absorb visible light from the wavelength converter converting radiations into visible light, and to convert the absorbed visible light into an electrical signal can be used. As such an element, for example, a positive-intrinsic-negative (PIN) type photoelectric conversion element including a P-layer doped with acceptor impurities, an I-layer serving as an intrinsic semiconductor layer, and an N-layer doped with donor impurities is available.

Another exemplary element is a metal-insulator-semiconductor (MIS) type photoelectric conversion element including a substrate, a thin film metal layer deposited on the substrate, an insulation layer deposited on the thin film metal layer composed of an amorphous silicon nitride preventing an electron and a positive hole from passing therethrough, a photoelectric conversion layer deposited on the insulation layer and composed of an amorphous silicon hydride, an N-type implantation-preventing layer deposited on the photoelectric conversion layer and preventing implantation of a positive hole, and a conductive layer deposited on the plantation-preventing layer. In the MIS-type photoelectric conversion element, the conductive layer can be transparent or can be deposited on a part of the implantation-preventing layer. Any of these photoelectric conversion elements can be used with a wavelength converter (e.g., made of $Gd_2O_2S$, $Gd_2O_3$, or CsI). Also, a conversion element configured to contain an amorphous selenium, a gallium arsenide, a lead iodide, or a mercury iodide and to absorb illuminated radiations and directly convert the radiations into an electrical signal can be used, or any similar material that can convert radiation into an electrical signal as known by one of ordinary skill in the relevant art.

The reading circuit is also not particularly limited to having a particular structure. For example, a reading circuit can include an amplification device configured to amplify a signal read from the conversion circuit unit, an accumulation device configured to accumulate the signal amplified by the amplification device, and a serial conversion device configured to serially convert the signal accumulated by the accumulating device can be used.

Each of the exemplary embodiments can be achieved by allowing a computer to execute its program. Also, a device for supplying the program to the computer (e.g., a computer-readable recording medium such as a CD-ROM), having such a program recorded therein or a transmission medium such as Internet, configured to transmit such a program is regarded as another exemplary embodiment. In addition, the above-described program can be regarded as another exemplary embodiment. The above-described program, recording medium, transmission medium, and program product fall in the scope of at least one exemplary embodiment.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

What is claimed is:

1. A radiography apparatus comprising:
a conversion circuit unit including a plurality of conversion elements arranged in a row-column pattern and configured to convert radiations into an electrical signal;
a drive circuit configured to control the driving of the conversion circuit unit, wherein, in an object-image reading operation, the conversion circuit unit detects an object image based on illuminated radiations, and the drive circuit drives the conversion circuit unit so as to allow the conversion circuit unit to output a signal based on the object image, and, in an offset-data reading operation, the conversion circuit unit detects offset data in a period when the radiations are not illuminating, and the drive circuit drives the conversion circuit unit so as to allow the conversion circuit unit to output a signal based on the offset data, and wherein, when the numbers of lines driven concurrently by the drive circuit in the object-image reading operation is represented by n (equal to 1 or greater) and the numbers of lines driven concurrently by the drive circuit in offset-data reading operation is represented by m, the drive circuit controls the conversion circuit unit so as to satisfy the expression: n<m; and
a signal-processing unit configured to process the electrical signal outputted from the conversion circuit unit, wherein the signal-processing unit includes an offset data generating unit configured to generate the offset data from the signal, and the offset data generating unit corrects the offset data such that the accumulation time of the offset data agrees with that of the object image.

2. The radiography apparatus according to claim 1, wherein the drive circuit controls the conversion circuit unit such that, in the object-image reading operation, signals based on the object image from the conversion elements are outputted for every line and, in the offset-data reading operation, other signals based on the offset data from the conversion elements and corresponding to a plurality of lines are concurrently added to one another and read.

3. The radiography apparatus according to claim 1, wherein the drive circuit controls the conversion circuit unit such that, during periods of the object-image reading operation and the offset-data reading operation, electrical signals from the conversion elements, corresponding to a plurality of lines, are concurrently added to one another and read, and that the number of lines in which the electrical signals are added to one another during the period of the offset-data reading operation is greater than that during the period of the object-image reading operation.

4. The radiography apparatus according to claim 1, further comprising a reading circuit configured to read the electrical signal outputted from the conversion circuit unit.

5. A radiography apparatus according to claim 1, further comprising:
a radiation source configured to emit radiations;
a control unit configured to control the radiography apparatus, wherein the control unit controls the drive circuit and the conversion circuit unit such that a period of the offset-data reading operation is shorter than that of the object-image reading operation.

6. An image processing method of a radiography apparatus, comprising:
a step of performing an object-image reading operation in which a conversion circuit unit detects an object image based on illuminated radiations and a drive circuit drives the conversion circuit unit so as to allow the conversion unit to output a signal based on the object image, and
a step of performing an offset-data reading operation in which the conversion circuit unit detects offset data in a period where there is no illuminated radiations, and the drive circuit drives the conversion circuit unit so as to allow the conversion unit to output a signal based on the offset data, wherein, when the numbers of lines driven concurrently by the drive circuit in the step of performing the object-image reading operation and the step of performing the offset-data reading operation are respectively represented by n (equal to 1 or greater) and m, the expression: n<m is satisfied, and
a step of performing an offset-data correcting operation in which a signal-processing unit configured to process an electrical signal outputted from the conversion circuit unit corrects the offset data such that the accumulation time of the offset data agrees with that of the object image.

7. A computer-readable storage medium storing a program instructing a computer to execute control of a radiography system, wherein the computer instructs a radiography apparatus to execute a step of performing an object-image reading operation in which a conversion circuit unit detects an object image based on illuminated radiations and a drive circuit drives the conversion circuit unit so as to allow the conversion unit to output a signal based on the object image, and a step of performing an offset-data reading operation in which the conversion circuit unit detects offset data in a period when there is no illuminated radiations, and the drive circuit drives the conversion circuit unit so as to allow the conversion unit to output a signal based on the offset data, wherein, when the numbers of lines driven concurrently by the drive circuit in the step of performing the object-image reading operation and the step of performing the offset-data reading operation are respectively represented by n (equal to 1 or greater) and m, the expression: n<m is satisfied, and a step of performing an offset-data correcting operation in which a signal-processing unit configured to process an electrical signal outputted from the conversion circuit unit corrects the offset data such that the accumulation time of the offset data agrees with that of the object image.

* * * * *